US012114761B2

(12) United States Patent
Porter (10) Patent No.: US 12,114,761 B2
(45) Date of Patent: Oct. 15, 2024

(54) APPARATUS CAPABLE OF TRANSFORMING BETWEEN A SLEEP AID AND A TOTE BAG

(71) Applicant: Selena Porter, Las Vegas, NV (US)

(72) Inventor: Selena Porter, Las Vegas, NV (US)

( * ) Notice: Subject to any disclaimer, the term of this patent is extended or adjusted under 35 U.S.C. 154(b) by 112 days.

(21) Appl. No.: 17/952,137

(22) Filed: Sep. 23, 2022

(65) Prior Publication Data

US 2023/0085857 A1 Mar. 23, 2023

Related U.S. Application Data

(63) Continuation-in-part of application No. 29/841,822, filed on Jun. 8, 2022.

(60) Provisional application No. 63/247,619, filed on Sep. 23, 2021.

(51) Int. Cl.
*A45F 4/08* (2006.01)

(52) U.S. Cl.
CPC ............ *A45F 4/08* (2013.01); *A45F 2200/05* (2013.01)

(58) Field of Classification Search
CPC ..... A45F 4/08; A45F 2200/05; A47G 9/0215; A47G 9/00; A47G 9/1036; A47G 9/1045; A47G 9/10
See application file for complete search history.

(56) References Cited

U.S. PATENT DOCUMENTS

| 4,679,263 A * | 7/1987 | Honer ................. A47G 9/1045 5/639 |
| 4,991,245 A | 2/1991 | Franco |
| 5,884,331 A * | 3/1999 | Barajas .................. A41D 15/04 5/636 |
| 6,493,891 B1 | 12/2002 | Livingston |
| 6,519,796 B2 | 2/2003 | Sloot |
| 6,523,354 B1 * | 2/2003 | Tolbert ....................... A61F 7/10 607/108 |
| 6,764,134 B1 * | 7/2004 | Crescenzi .............. A47C 31/00 297/219.12 |
| 8,893,332 B2 | 11/2014 | Kavovit |
| 2010/0089897 A1 * | 4/2010 | Bart ........................ A61F 7/034 2/243.1 |
| 2010/0139001 A1 * | 6/2010 | Mangano ............. A47G 9/1045 297/229 |

(Continued)

FOREIGN PATENT DOCUMENTS

WO WO2002082941 A1 10/2002

*Primary Examiner* — Fredrick C Conley (57) ABSTRACT

An apparatus capable of transforming between a sleep aid and a tote bag is an apparatus that can be used to help the user to carry various personal objects while travelling. The apparatus can also be used for comfort while the user rests during the travel. To do so, the apparatus includes a tote bag, a plurality of heating devices, and a controller. The tote bag is a transformable structure that can be configured to be used as a storage structure or as a pillow-blanket combination. The tote bag also facilitates the transformation of the apparatus between the two configurations by the user on-the-go. The plurality of heating devices provides warm and comfort to the user when the user utilizes the apparatus as a pillow-blanket combination. The controller enables the user to control the operation of the plurality of heating devices while utilizing the apparatus as a pillow-blanket combination.

15 Claims, 10 Drawing Sheets

(56) References Cited

U.S. PATENT DOCUMENTS

| | | | | |
|---|---|---|---|---|
| 2012/0005801 A1* | 1/2012 | Parr | ......................... | A41D 3/00 2/84 |
| 2015/0082515 A1* | 3/2015 | Parziale | ................ | A47C 7/383 2/173 |
| 2020/0323689 A1* | 10/2020 | Morshed | .............. | A47G 9/1081 |

* cited by examiner

APPARATUS CAPABLE OF TRANSFORMING BETWEEN A SLEEP AID AND A TOTE BAG

The current application is a continuation-in-part (CIP) application of the U.S. design application Ser. No. 29/841,822 filed on Jun. 8, 2022.

The current application also claims a priority to a U.S. provisional application Ser. No. 63/247,619 filed on Sep. 23, 2021.

FIELD OF THE INVENTION

The present invention relates generally to multi-purpose devices and travel accessories. More specifically, the present invention provides a multi-purpose travel apparatus that can be configured to be used as a tote bag to store and carry objects or as a pillow-blanket combination to provide comfort to the user.

BACKGROUND OF THE INVENTION

Nowadays, travelling is a common activity for many people for different purposes, such as for business or pleasure. For those who travel frequently, the inconveniences associated with travelling are very familiar. For example, limitations on the amount one can bring aboard an airplane are often strict, and one may want to avoid paying additional costs to check luggage that one was intending to bring on board the airplane. Additionally, there are often flight delays that leave travelers in an airport for hours at a time. A simple way to pass this time would be to sleep for a short duration, but airports hardly foster an environment that makes sleeping feasible. Travelers often use items like extra clothes and luggage to sleep on the floor of the airport gate, although it is hardly ever a comfortable or enjoyable experience. In addition, the extra items can add to the luggage the traveler needs to carry.

Therefore, an objective of the present invention is to provide a multi-purpose apparatus capable of being configured as a tote bag or as a pillow-blanket combination. The present invention enables the user to carry any desired objects inside an apparatus that can also be configured to be used for comfort. Another objective of the present invention is to provide a multi-purpose apparatus that provides different comforting features integrated into the apparatus. The present invention includes a heating mechanism to foster a more comfortable experience when using the present invention as a pillow-blanket combination. Another objective of the present invention is to provide a multi-purpose apparatus that can be easily transformed between the different configurations. The present invention can be easily transformed on-the-go without the use of external tools. Additional features and benefits of the present invention are further discussed in the sections below.

SUMMARY OF THE INVENTION

The present invention is an apparatus capable of being transformed between a sleep aid and a tote bag. The present invention is designed to be transformable by the user on-the-go without the need of external tools. In one configuration, the present invention can be used as a tote bag to carry different objects the user needs while travelling. In a second configuration, the present invention can be used as a pillow-blanket combination to provide comfort to the user. The present invention can be transformed from the storage configuration to the pillow-blanket configuration by simply reversing apparatus. This way, the user can simply transform the apparatus on-the-go to suit the user's needs without requiring additional accessories.

The present invention is also equipped with various comfort features that increase the comfort of the user while utilizing the apparatus in the pillow-blanket configuration. The comfort features can include, but are not limited to, a heating mechanism that keeps the user warm while utilizing the apparatus in the pillow-blanket configuration. In addition, the present invention can provide a chin strap and an eye mask to help secure the apparatus to the user and to cover the eyes of the user while wearing the apparatus in the pillow-blanket configuration, respectively. Additional features can be included that increase the functionality of the present invention.

DETAIL DESCRIPTIONS OF THE INVENTION

All illustrations of the drawings are for the purpose of describing selected versions of the present invention and are not intended to limit the scope of the present invention.

The present invention is an apparatus capable of being transformed between a sleep aid and a tote bag. The present invention can be used to help the user carry small desired objects while travelling. The present invention can also be used for comfort while the user rests during the travel. As can be seen in FIGS. 1 through 8, the present invention comprises a tote bag 1, a plurality of heating devices 15, and a controller 20. The tote bag 1 is a transformable structure that can be configured to be used as a storage structure or as a pillow-blanket combination. The tote bag 1 also facilitates the transformation of the present invention between the two configurations by the user on-the-go. The plurality of heating devices 15 provides warm and comfort to the user when the user utilizes the present invention as a pillow-blanket combination. The controller 20 enables the user to control the operation of the plurality of heating devices 15 while utilizing the present invention as a pillow-blanket combination.

The general configuration of the aforementioned components enables the user to carry the necessary accessories to have comfort while travelling without carrying too many objects that add weight to the luggage of the user. As can be seen in FIGS. 1 through 8, the tote bag 1 is designed as a reversible structure able to accommodate all the accessories required for the present invention to be used as a pillow-blanket combination. Accordingly, the tote bag 1 comprises a bag body 2, a first wrap panel 9, a second wrap panel 10, and a neck pillow 11. The bag body 2 corresponds to the structure that enables the present invention to be used as a tote bag 1 for storage. The first wrap panel 9 and the second wrap panel 10 enable the present invention to be used as a blanket. The neck pillow 11 adds comfort so that the present invention can be used as a pillow-blanket combination. Further, the bag body 2 comprises a proximal bag panel 3, a distal bag panel 4, a first lengthwise edge 5, a second lengthwise edge 6, a widthwise opening 7, and a widthwise edge 8. The proximal bag panel 3 and the distal bag panel 4 are two elongated panels that form the bag structure of the bag body 2. The first lengthwise edge 5 and the second lengthwise edge 6 correspond to the longest edges of the bag body 2. The widthwise edge 8 corresponds to one of the shortest edges of the bag body 2, while the widthwise opening 7 corresponds to the other short edge that has been left unconnected to form the widthwise opening 7.

As can be seen in FIGS. 1 through 10, to form the tote bag 1, the first lengthwise edge 5 and the second lengthwise edge 6 are positioned opposite to each other about the bag body 2 due to the overall rectangular shape of the bag body 2. To secure the proximal bag panel 3, the distal bag panel 4, and the first wrap panel 9 together, the proximal bag panel 3, the distal bag panel 4, and the first wrap panel 9 are connected along the first lengthwise edge 5. Similarly, the proximal bag panel 3, the distal bag panel 4, and the second wrap panel 10 are connected along the second lengthwise edge 6 to secure the proximal bag panel 3, the distal bag panel 4, and the second wrap panel 10 together. Further, the widthwise opening 7 and the widthwise edge 8 are positioned opposite to each other about the bag body 2 due to the overall rectangular shape of the bag body 2. In addition, to secure the proximal bag panel 3, the distal bag panel 4, and the neck pillow 11 together, the proximal bag panel 3, the distal bag panel 4, and the neck pillow 11 are connected along the widthwise edge 8. Furthermore, the plurality of heating devices 15 is integrated throughout the tote bag 1 to generate warmth for the user when the user is wearing the present invention as a pillow-blanket combination. In addition, to help the user control the operation of the plurality of heating devices 15, the controller 20 is electronically connected to each of the plurality of heating devices 15. The controller 20 enables the user to power up the heating devices individually or as a group as well as to control the intensity of each of the heating devices. So, the controller 20 can include different buttons as well as indicators that help the user control the operation of the plurality of heating devices 15 as well as to monitor the operation of the plurality of heating devices 15.

As previously discussed, the present invention can be transformed by the user to utilize the present invention as a storage device or as a pillow-blanket combination. As can be seen in FIGS. 6 through 8 and 10, in a pillow-blanket configuration, the first wrap panel 9, the second wrap panel 10, the neck pillow 11, and the controller 20 are positioned outside the bag body 2. In the pillow-blanket configuration, the first wrap panel 9 and the second wrap panel 10 can be fully extended so that each wrap panel can be wrapped around the body of the user. The bag body 2 is arranged to cover the back of the user once the first wrap panel 9 and the second wrap panel 10 are wrapped around the user. Further, the neck pillow 11 can be positioned behind the user's neck so that user's head can comfortably rest on the neck pillow 11. Further, the controller 20 is positioned external to the bag body 2 so that the controller 20 is accessible to the user to control the operation of the plurality of heating devices 15. Furthermore, the first wrap panel 9, the second wrap panel 10, the neck pillow 11, and the interior surfaces of the proximal bag panel 3 and the distal bag panel 4 can be covered or made from a soft material including, but not limited to, fleece material that adds comfort and warmth to the user when using the present invention in the pillow-blanket configuration. On the other hand, the exterior surfaces of the proximal bag panel 3 and the distal bag panel 4 can be covered or made from more durable materials including, but not limited to, weatherproof fabric or leather that increase the durability of the bag body 2.

As can be seen in FIGS. 1 through 5, in a storage configuration, the first wrap panel 9, the second wrap panel 10, the neck pillow 11, and the controller 20 are positioned inside the bag body 2. In the storage configuration, the first wrap panel 9, the second wrap panel 10, the neck pillow 11, and the controller 20 are stored within the bag body 2 so that the bag body 2 can be carried as a traditional bag. Further, the bag body 2 has a size large enough to receive other objects, such as sunglasses or a book, in addition to the first wrap panel 9, the second wrap panel 10, the neck pillow 11, and the controller 20. To transform the present invention from the pillow-blanket configuration to the storage configuration, the user can reach into the bag body 2 and grab onto the widthwise edge 8. Then, the user pulls the widthwise edge 8 to reverse the bag body 2, which also moves the first wrap panel 9, the second wrap panel 10, the neck pillow 11, and the controller 20 inside the reversed bag body 2. Similarly, to transform the present invention from the storage configuration to the pillow-blanket configuration, the user reaches into the bag body 2 and grabs onto the widthwise edge 8. Then, the user pulls the widthwise edge 8 to reverse the bag body 2, which also moves the first wrap panel 9, the second wrap panel 10, the neck pillow 11, and the controller 20 outside the bag body 2. In other embodiments, the present invention can utilize different mechanisms that allow the transformation of the present invention between the different configurations or allow for additional configurations.

Figure 1:
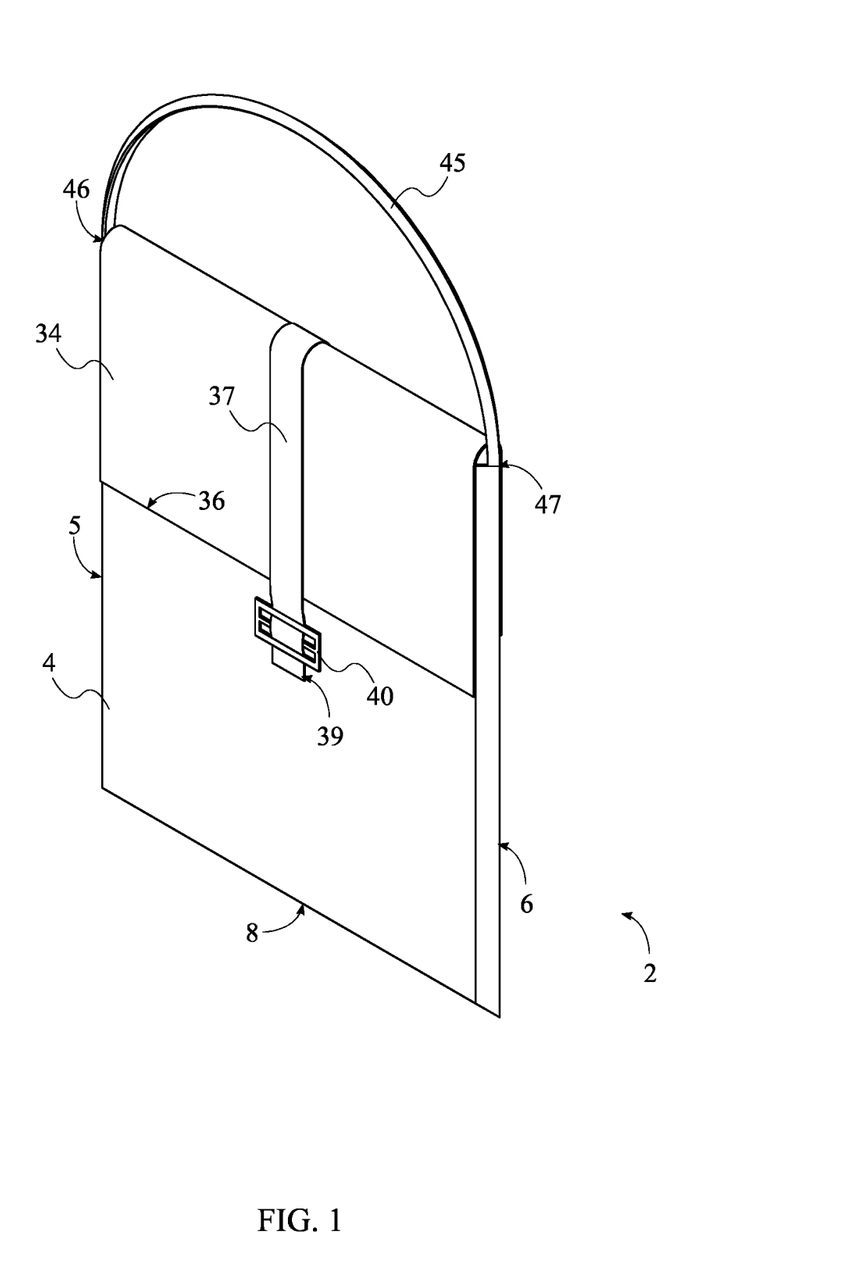
FIG. 1 is a top-front-perspective view of the present invention, wherein the present invention is shown in a storage configuration.
Figure 2:
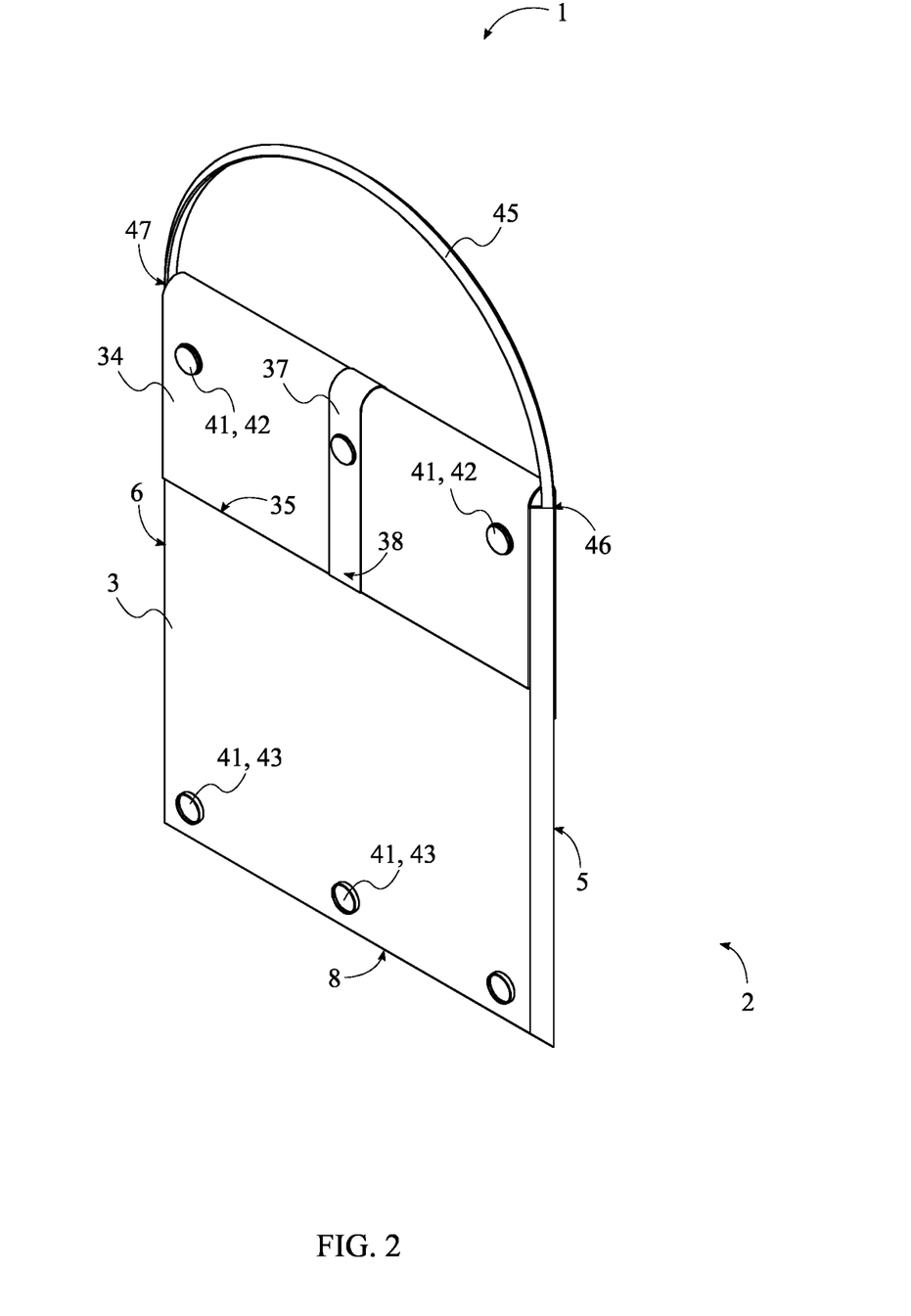
FIG. 2 is a top-rear-perspective view of the present invention, wherein the present invention is shown in the storage configuration.
Figure 3:
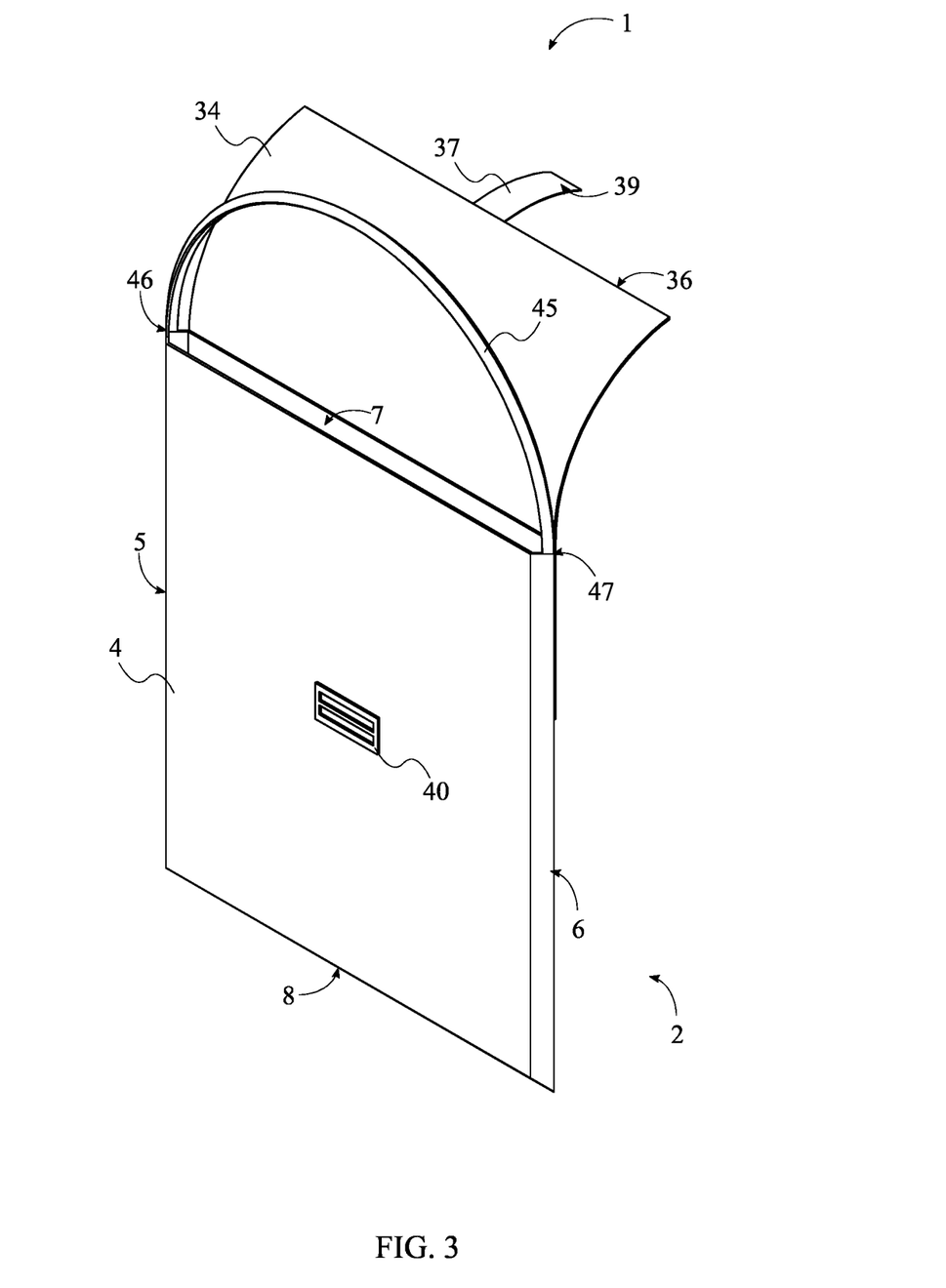
FIG. 3 is a top-front-perspective view of the present invention, wherein a closure flap is shown opened in the storage configuration.
Figure 4:
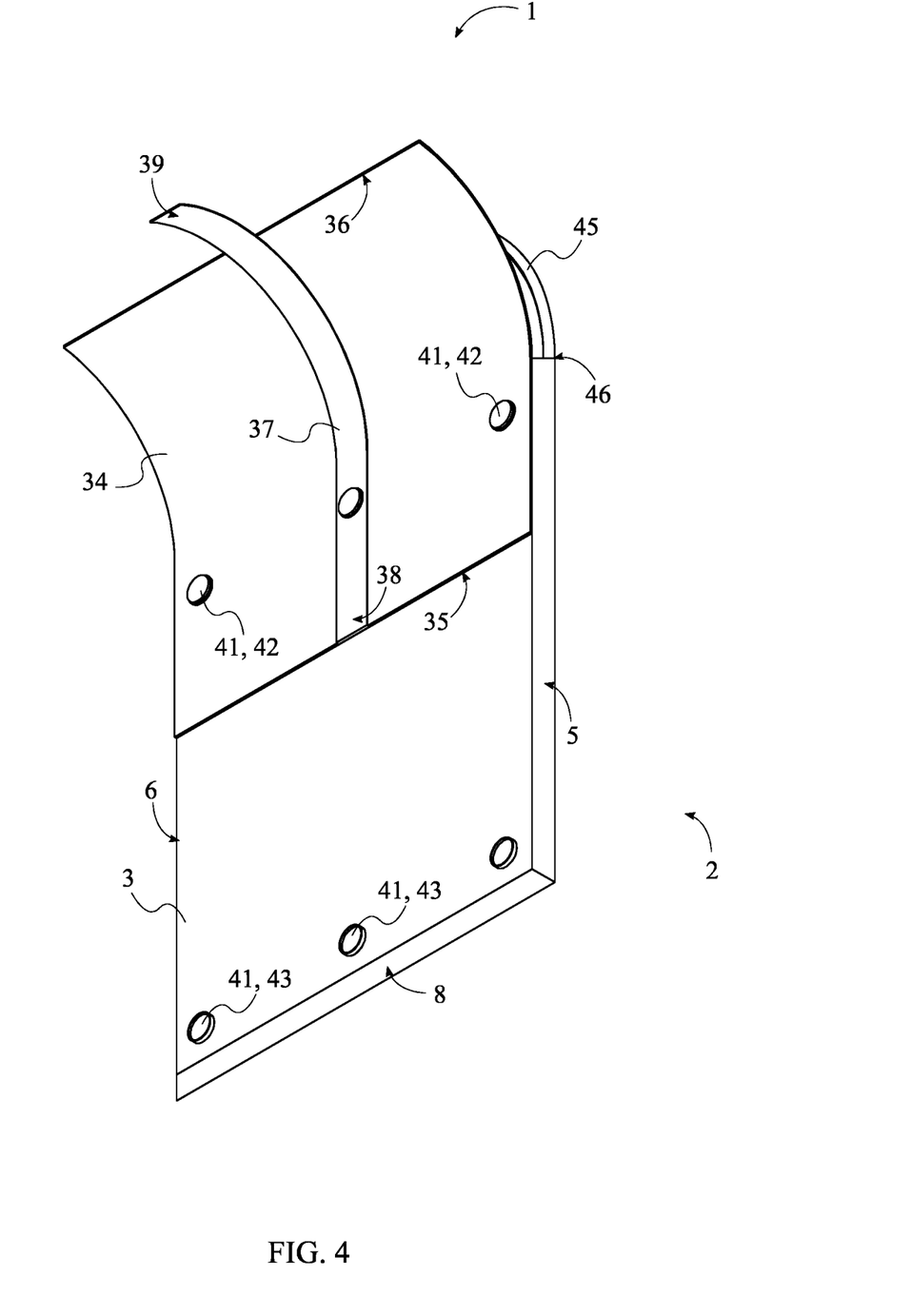
FIG. 4 is a bottom-rear-perspective view of the present invention, wherein the closure flap is shown opened in the storage configuration.
Figure 5:
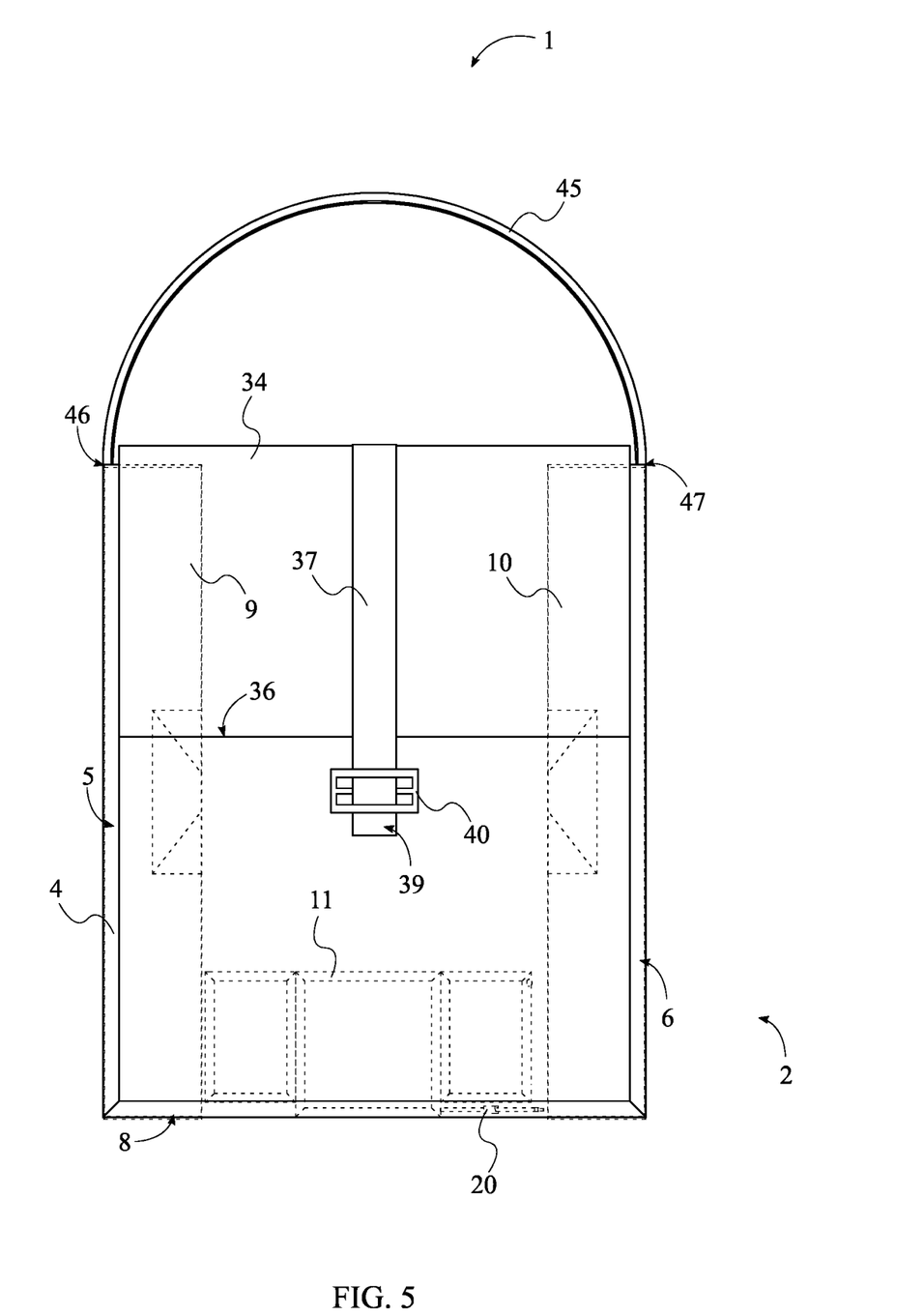
FIG. 5 is a front schematic view of the present invention, wherein a first wrap panel, a second wrap panel, a neck pillow, and a controller are shown stored within the bag body in the storage configuration.
Figure 6:
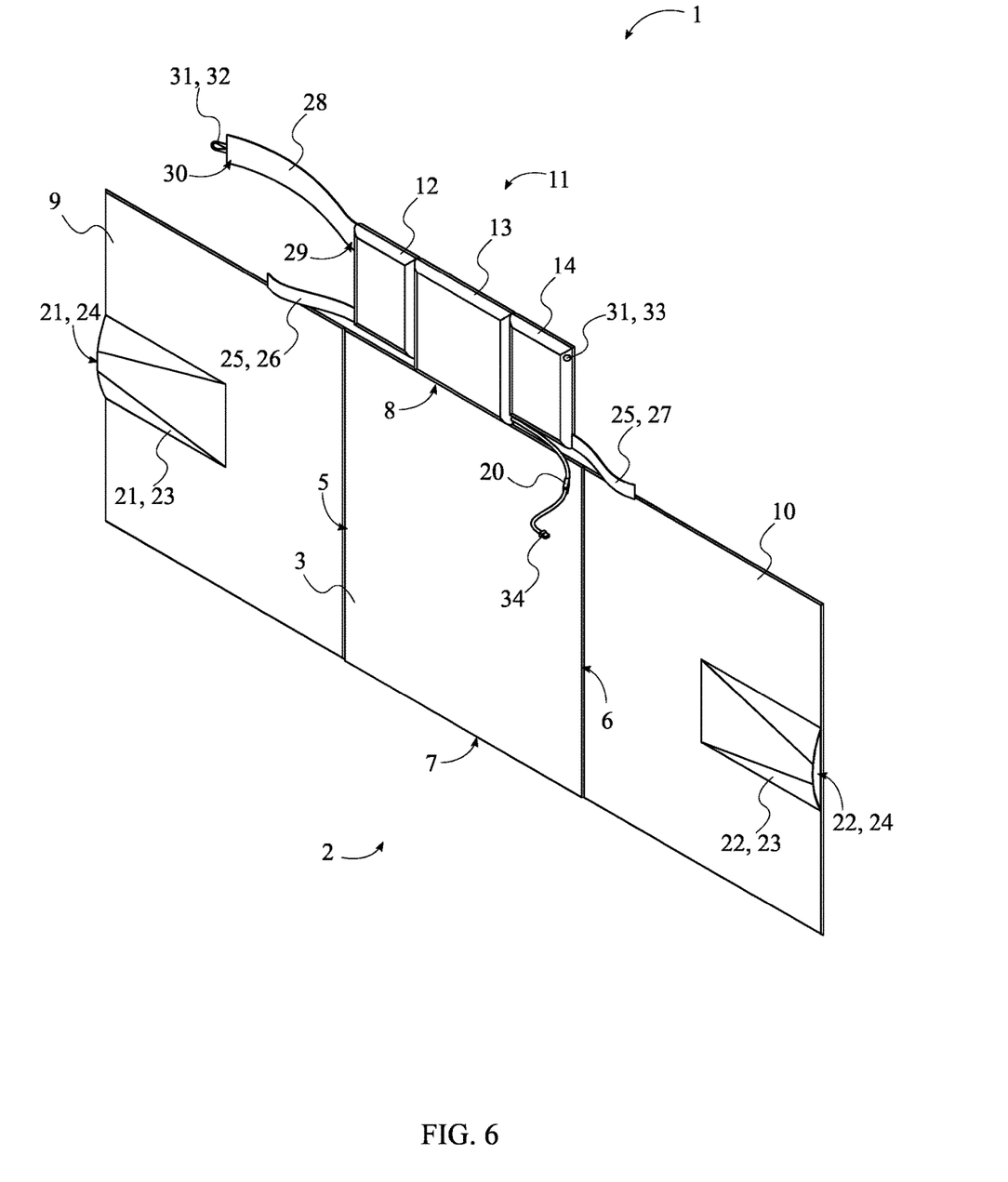
FIG. 6 is a top-front-perspective view of the present invention, wherein the first wrap panel, the second wrap panel, the neck pillow, and the controller are shown positioned outside the bag body in a pillow-blanket configuration.
Figure 7:
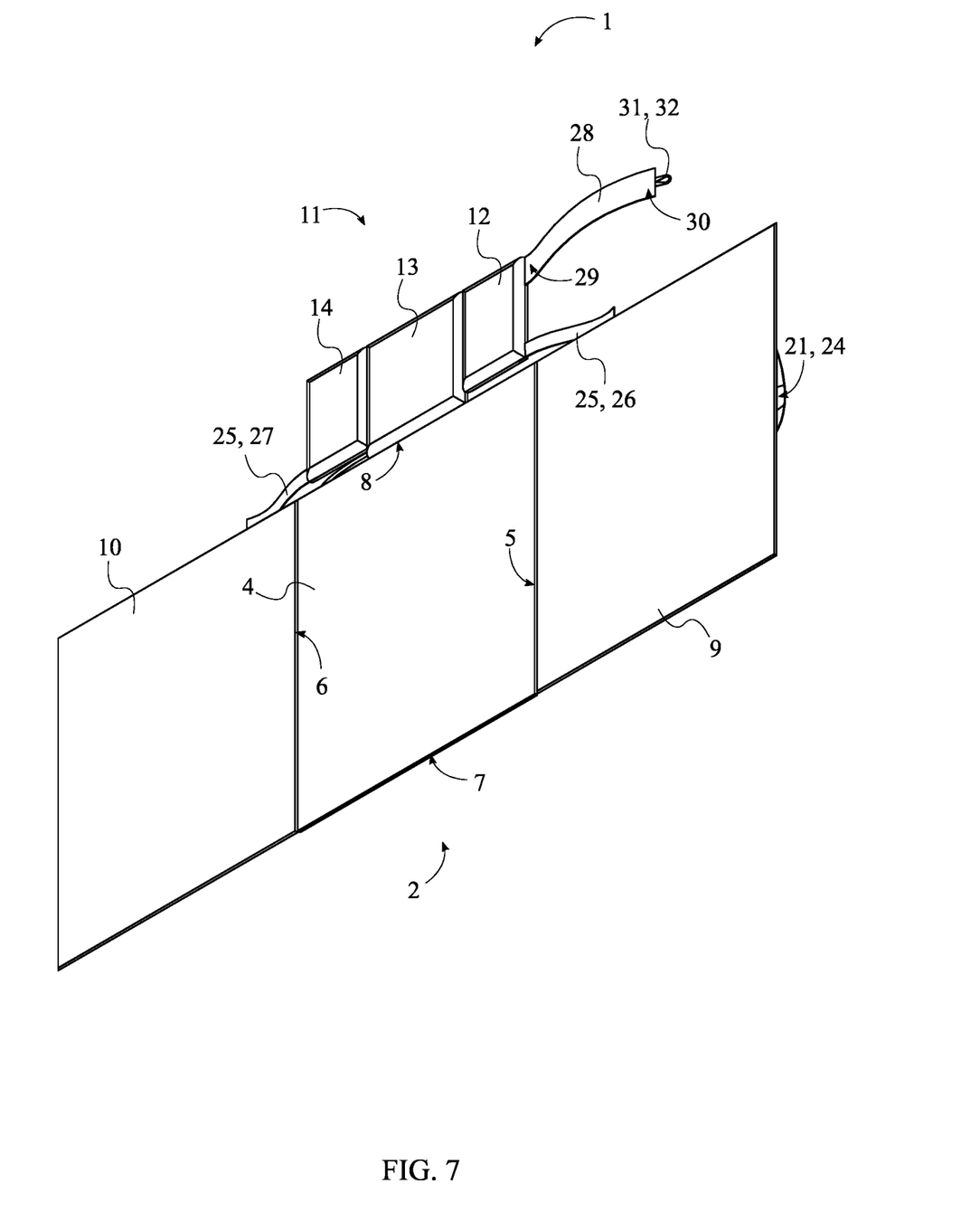
FIG. 7 is a bottom-rear-perspective view of the present invention, wherein the present invention is shown in the pillow-blanket configuration.
Figure 8:
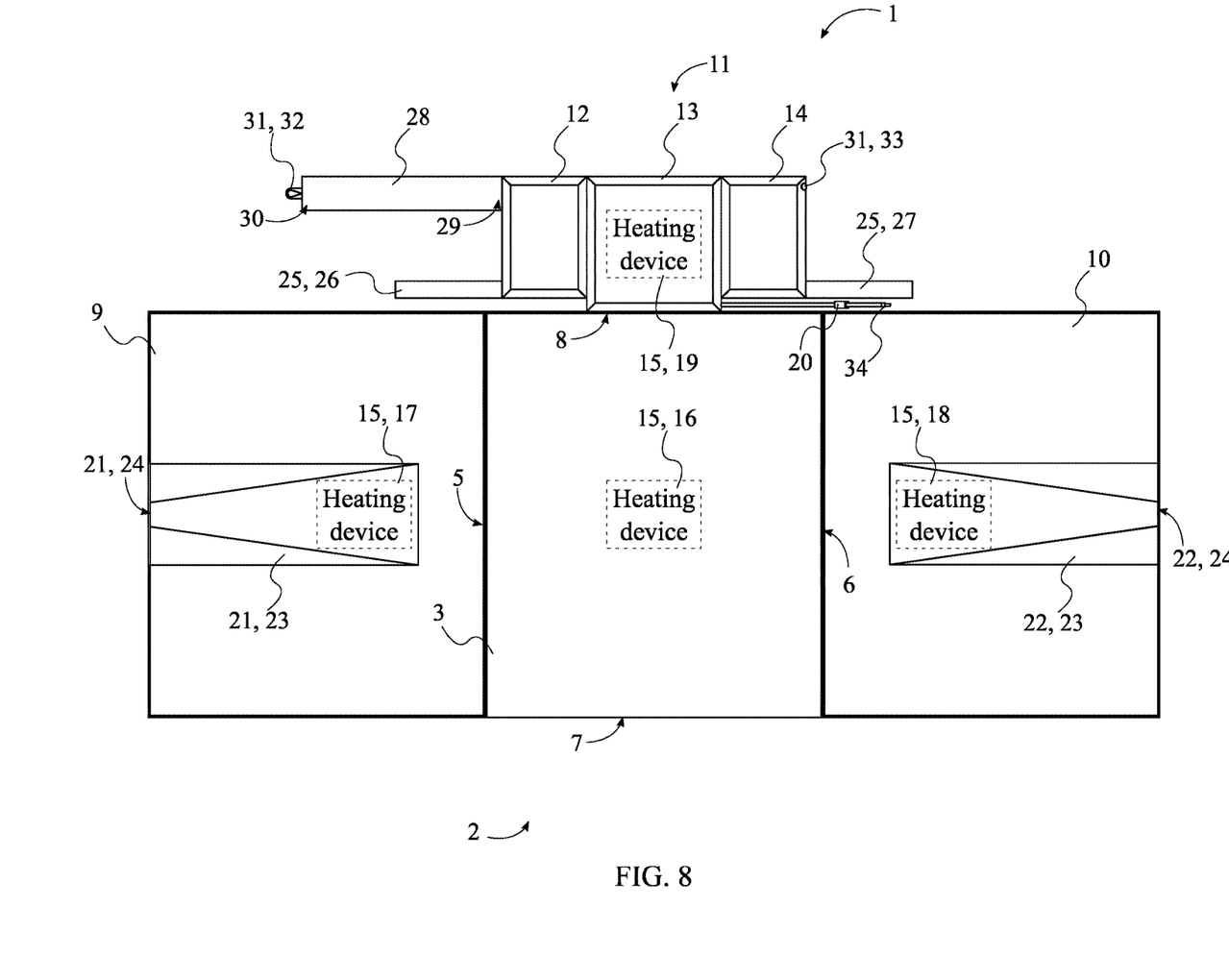
FIG. 8 is a front schematic view of the present invention, wherein a plurality of heating devices is shown distributed across the tote bag.

As can be seen in FIGS. 6 through 8, to further add comfort to the user while wearing the present invention in the pillow-blanket configuration, the present invention may further comprise a first hand-receiving pocket 21 and a second hand-receiving pocket 22. The first hand-receiving pocket 21 and the second hand-receiving pocket 22 enable the user to cover the user's hands while the first wrap panel 9 and the second wrap panel 10 are wrapped around the user's body. This way, the user does not have to hold onto the wrap panels but instead comfortably position the user's hands inside the hand-receiving pockets. To do so, the first hand-receiving pocket 21 and the second hand-receiving pocket 22 each comprises a pocket body 23 and a pocket opening 24. The pocket body 23 is the space where the hand can be placed, while the pocket opening 24 enables the insertion of the hand into the pocket body 23. The pocket body 23 of the first hand-receiving pocket 21 is integrated into the first wrap panel 9. The pocket body 23 of the first hand-receiving pocket 21 is also positioned adjacent to the corresponding heating device of the first wrap panel 9 so that the user's hand is kept warm. In addition, the pocket opening 24 of the first hand-receiving pocket 21 and the first lengthwise edge 5 are positioned opposite to each other across the first wrap panel 9. This way, when the user wraps the first wrap panel 9 around the user's body, the user can position the opposite hand into the first hand-receiving pocket 21. Similarly, the pocket body 23 of the second hand-receiving pocket 22 is integrated into the second wrap panel 10. The pocket body 23 of the second hand-receiving pocket 22 is also positioned adjacent to the corresponding heating device of the second wrap panel 10 so that the user's hand is kept warm. Further, the pocket opening 24 of the second hand-receiving pocket 22 and the second lengthwise edge 6 are positioned opposite to each other across the second wrap panel 10. This way, when the user wraps the second wrap panel 10 around the user's body, the user can position the opposite hand into the second hand-receiving pocket 22. In other embodiments, additional pockets can be provided throughout the tote bag 1 to store different items.

To add comfort to the user's head, the neck pillow 11 is designed to wrap around the user's neck. As can be seen in FIGS. 6 through 8, the neck pillow 11 may comprise a first side cushioning section 12, a center cushioning section 13, and a second side cushioning section 14. The first side cushioning section 12, the center cushioning section 13, and the second side cushioning section 14 are arranged to be positioned around the user's neck to support the user's neck more comfortably. Accordingly, the center cushioning section 13 is hingedly connected along the widthwise edge 8 to secure the center cushioning section 13 to the bag body 2. The first side cushioning section 12 is hingedly connected adjacent to the center cushioning section 13 to secure the first side cushioning section 12 to the center cushioning section 13. Likewise, the second side cushioning section 14 is hingedly connected adjacent to the center cushioning section 13, opposite to the first side cushioning section 12, to secure the second side cushioning section 14 to the center cushioning section 13. This way, when the user positions the neck pillow 11 around the user's neck, the center cushioning section 13 can be positioned on the back of the neck while the first side cushioning section 12 and the second side cushioning section 14 are positioned on the opposite sides of the neck. Thus, the user's head is more comfortably supported by the neck pillow 11.

In order to secure the positioning of the neck pillow 11 around the user's neck, the present invention may further comprise a chin strap 25. As can be seen in FIGS. 6 through 8 and 10, the chin strap 25 is designed to comfortably secure the positioning of the first side cushioning section 12, the center cushioning section 13, and the second side cushioning section 14 around the users' neck. To do so, the chin strap 25 comprises a first strap section 26 and a second strap section 27. The first strap section 26 and the second strap section 27 are strap sections of equal length that can be fastened around the user's neck in a safe and comfortable manner. The first strap section 26 is terminally connected to the first side cushioning section 12, opposite to the center cushioning section 13, to secure the first strap section 26 to the first side cushioning section 12. Likewise, the second strap section 27 is terminally connected to the second side cushioning section 14, opposite to the center cushioning section 13, to secure the second strap section 27 to the second side cushioning section 14. This way, when the first side cushioning section 12 and the second side cushioning section 14 are positioned on the sides of the neck, the user ties the free ends of the first strap section 26 and the second strap section 27 together to keep the first side cushioning section 12 and the second side cushioning section 14 securely and safely in place.

In addition to the neck pillow 11, the present invention may further comprise an eye mask 28 that helps the user rest while wearing the present invention in the pillow-blanket configuration. As can be seen in FIGS. 6 through 8 and 10, the present invention may also comprise a mask fastening mechanism 31 that helps the user secure the eye mask 28 in place while the user is resting. To do so, the eye mask 28 comprises a first mask end 29 and a second mask end 30 corresponding to the terminal ends of the eye mask 28. The mask fastening mechanism 31 comprises a first interlocking piece 32 and a second interlocking piece 33 that can be coupled together to secure the eye mask 28 in place. The first interlocking piece 32 can be a loop, while the second interlocking piece 33 can be a button that can be inserted into the loop. Accordingly, the first mask end 29 is connected onto the first side cushioning section 12, opposite to the center cushioning section 13 to secure the eye mask 28 to the first side cushioning section 12. This way, the user does not risk losing the eye mask 28 by accident. Further, the first interlocking piece 32 is connected onto the second mask end 30, while the second interlocking piece 33 is connected onto the second side cushioning section 14, opposite to the center cushioning section 13. This way, once the user has accommodated the neck pillow 11 around the user's neck, the user can position the eye mask 28 around the user's eyes and then secure the eye mask 28 in place by engaging the first interlocking piece 32 with the second interlocking piece 33. In other embodiments, the mask fastening mechanism 31 may include different fastening mechanisms that enables the user to removably fasten the eye mask 28 as desired.

As can be seen in FIGS. 1 through 5, the present invention may further comprise a closure flap 34 that enables the user to seal the bag body 2 to keep all items inside the bag body 2 during the storage configuration. To do so, the closure flap 34 comprises a fixed flap edge 35 and a free flap edge 36. The closure flap 34 is preferably a shorter piece of material of sizes matching the width of the bag body 2 and a length large enough to cover the widthwise opening 7. Accordingly, the fixed flap edge 35 and the free flap edge 36 are positioned opposite to each other across the closure flap 34 due to the overall rectangular shape of the closure flap 34. The fixed flap edge 35 is connected onto the proximal bag panel 3, adjacent to the widthwise opening 7, while the free flap edge 36 can be positioned over the distal bag panel 4 so that the closure flap 34 covers the widthwise opening 7.

As can be seen in FIGS. 1 through 5, to fasten the closure flap 34 to the bag body 2, the present invention may further comprise a flap strap 37 and a strap-receiving buckle 40. The flap strap 37 and the strap-receiving buckle 40 enable the fastening of the closure flap 34 to the bag body 2 to prevent the closure flap 34 from accidentally exposing the widthwise opening 7 when the present invention is being transported. To do so, the flap strap 37 comprises a fixed strap end 38 and a free strap end 39 corresponding to the terminal ends of the flap strap 37. Further, the fixed strap end 38 is connected onto the proximal bag panel 3, adjacent to the fixed flap edge 35, to secure the flap strap 37 to the bag body 2. The strap-receiving buckle 40 is also connected onto the distal bag panel 4, adjacent to the widthwise opening 7, to secure the strap-receiving buckle 40 to the bag body 2. This way, when the user wants to fasten the closure flap 34, the user slidably engages the free strap end 39 with the strap-receiving buckle 40 to fasten the free flap edge 36 to the distal bag panel 4. In other embodiments, different fastening mechanisms can be used to fasten the closure flap 34 to the bag body 2.

As previously discussed, the bag body 2 is large enough to receive various small items the user wants to carry along while travelling. However, the bag body 2 can also be shortened if the bag body 2 is mostly empty to save space. As can be seen in FIGS. 1 through 5, the present invention may further comprise a volumetric-reduction fastening mechanism 41. The volumetric-reduction fastening mechanism 41 enables the user to quickly reduce the size of the bag body 2 if desired. The volumetric-reduction fastening mechanism 41 comprises a plurality of first interlocking pieces 42 and a plurality of second interlocking pieces 43 that can be selectively engaged to reduce the overall size of the bag body 2. The plurality of first interlocking pieces 42 is connected across the proximal bag panel 3 in between the first lengthwise edge 5 and the second lengthwise edge 6. This way, the plurality of first interlocking pieces 42 covers the width of the bag body 2. The plurality of first interlocking pieces 42 is also positioned adjacent to the widthwise opening 7. Similarly, the plurality of second interlocking pieces 43 is connected across the proximal bag panel 3 in between the first lengthwise edge 5 and the second lengthwise edge 6. This way, the plurality of second interlocking pieces 43 also covers the width of the bag body 2. However, the plurality of second interlocking pieces 43 is positioned adjacent to the widthwise edge 8. Thus, when the user wants to reduce the overall size of the bag body 2, the user folds the bag body 2 by moving the widthwise edge 8 towards the widthwise opening 7 along the proximal bag panel 3. Then, the user engages each first interlocking piece of the plurality of first interlocking pieces 42 with a corresponding second interlocking piece of the plurality of second interlocking pieces 43 to lock the shortened bag body 2 in place. If the user wants to enlarge the bag body 2, the user simply releases the volumetric-reduction fastening mechanism 41 so that bag body 2 is released to return to the original size. In other embodiments, the present invention may utilize different mechanisms that enable the adjustment of the overall size of the bag body 2 for storage purposes.

As can be seen in FIGS. 6 through 9, to enable the operation of the plurality of heating devices 15, the present invention may further comprise a power terminal 44 that enables the user to utilize an external power source to power the plurality of heating devices 15. The power terminal 44 can include, but is not limited to, a power connector such as a Universal Serial Bus (USB) connector that can be plugged into a building's electrical system or an appropriate external power source to power the plurality of heating devices 15. To do so, the power terminal 44 is positioned offset to the controller 20 so that the power terminal 44 can reach the external power source without the user having to move around. In addition, the power terminal 44 is electrically connected to the controller 20 and each of the plurality of heating devices 15 to transmit the voltage necessary for the operation of the plurality of heating devices 15. In other embodiments, the present invention can include a portable power source such as, but not limited to, rechargeable batteries that enable the user to utilize the plurality of heating devices 15 without being close to an external power source.

Figure 9:
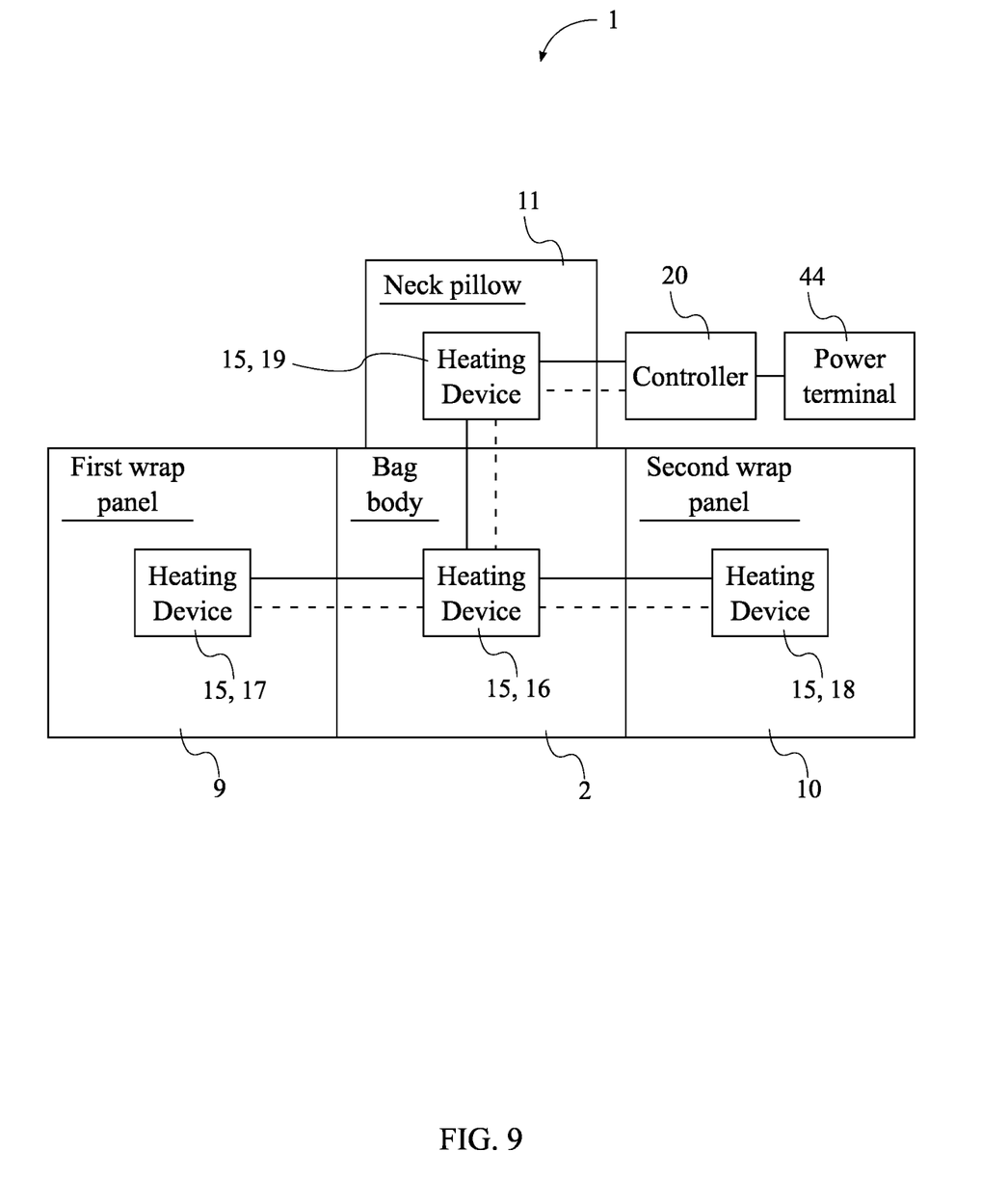
FIG. 9 is a schematic view of the electrical connections and the electronic connections of the present invention, wherein the electrical connections are shown in solid lines, and wherein the electronic connections are shown in dashed lines.
Figure 10:
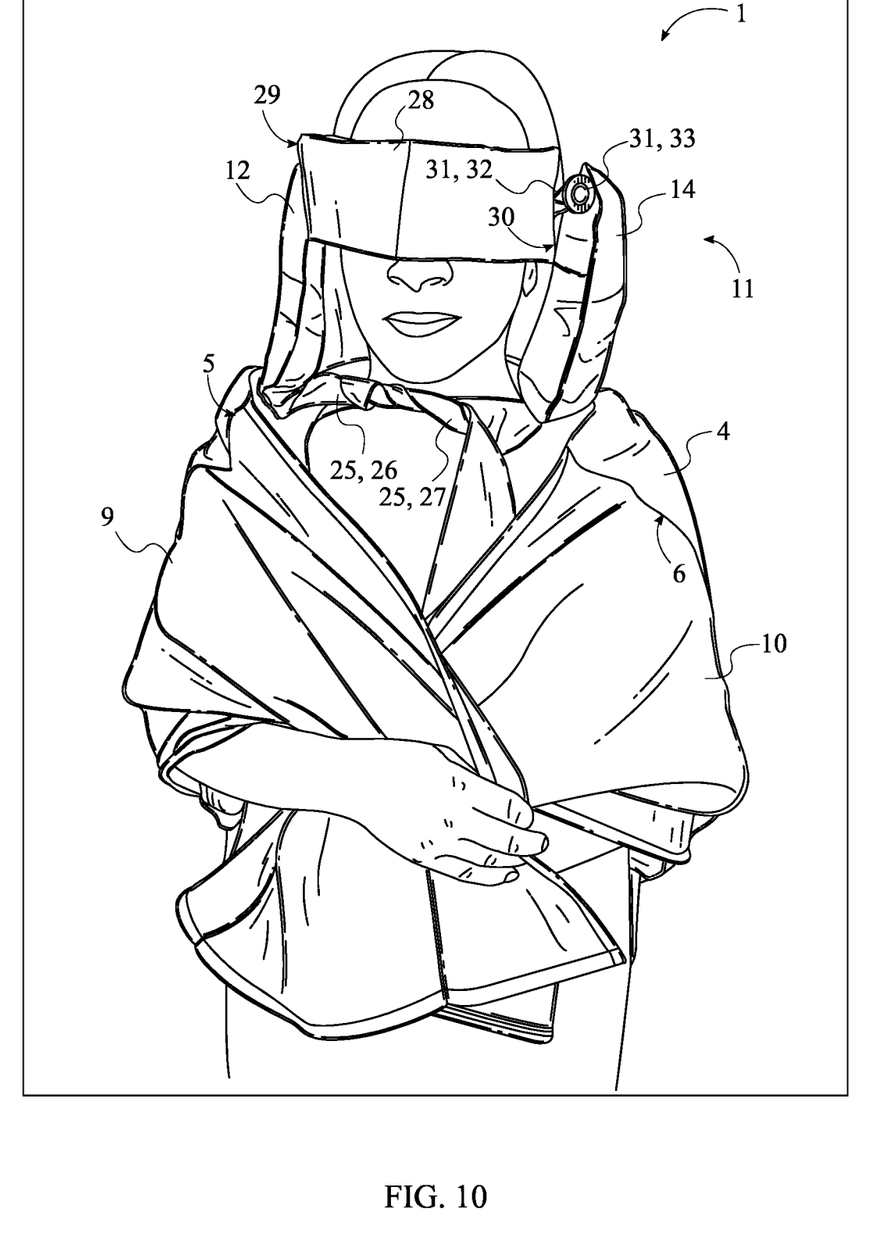
FIG. 10 is a top-front-perspective view of the present invention, wherein the present invention is shown worn by a user in the pillow-blanket configuration.

As can be seen in FIGS. 8 through 10, to ensure that the plurality of heating devices 15 provide the most warmth to the user while the user is wearing the present invention in the pillow-blanket configuration, the plurality of heating devices 15 includes several heating devices distributed across the first wrap panel 9, the second wrap panel 10, the neck pillow 11, and the bag body 2. Accordingly, the plurality of heating devices 15 may comprise a bag heating device 16, a first panel heating device 17, a second panel heating device 18, and a pillow heating device 19. The bag heating device 16 is integrated into the bag body 2 to warm the body area covered by the bag body 2. The first panel heating device 17 is integrated into the first wrap panel 9 to warm the body area covered by the first wrap panel 9. The second panel heating device 18 is integrated into the second wrap panel 10 to warm the body area covered by the second wrap panel 10. Further, the pillow heating device 19 is integrated into the neck pillow 11 to warm the user's neck. Thus, the user's body can be evenly warmed by the plurality of heating devices 15 when the user is wearing the present invention in the pillow-blanket configuration.

As can be seen in FIGS. 1 through 5, to enable the user to comfortably carry the present invention in the storage configuration, the present invention may further comprise a shoulder strap 45. The shoulder strap 45 enables the user to carry the present invention from the shoulder or by holding onto the shoulder strap 45 with one hand. To do so, the shoulder strap 45 comprises a first strap end 46 and a second strap end 47 corresponding to the terminal ends of the shoulder strap 45. The first strap end 46 is connected onto the bag body 2, adjacent to the first lengthwise edge 5 to secure the first strap end 46 to the bag body 2. Similarly, the second strap end 47 is connected onto the bag body 2, adjacent to the second lengthwise edge 6, to secure the second strap end 47 to the bag body 2. Further, the shoulder strap 45 is positioned across the widthwise opening 7. This way, when the present invention is in the storage configuration, the user can safely carry the present invention without worrying about items falling off the bag body 2 through the widthwise opening 7. In other embodiments, additional straps can be provided and arranged so that the present invention can be carried as a backpack or a longer strap so that the present invention can be carried as a satchel.

Although the invention has been explained in relation to its preferred embodiment, it is to be understood that many other possible modifications and variations can be made without departing from the spirit and scope of the invention.

What is claimed is:

1. An apparatus capable of transforming between a sleep aid and a tote bag comprising:
    a tote bag;
    a plurality of heating devices;
    a controller;
    the tote bag comprising a bag body, a first wrap panel, a second wrap panel, and a neck pillow;
    the bag body comprising a proximal bag panel, a distal bag panel, a first lengthwise edge, a second lengthwise edge, a widthwise opening, and a widthwise edge;
    the first lengthwise edge and the second lengthwise edge being positioned opposite to each other about the bag body;
    the proximal bag panel, the distal bag panel, and the first wrap panel being connected along the first lengthwise edge;

the proximal bag panel, the distal bag panel, and the second wrap panel being connected along the second lengthwise edge;
the widthwise opening and the widthwise edge being positioned opposite to each other about the bag body;
the proximal bag panel, the distal bag panel, and the neck pillow being connected along the widthwise edge;
the plurality of heating devices being integrated throughout the tote bag;
the controller being electronically connected to each of the plurality of heating devices; and
the bag body, the first wrap panel, the second wrap panel, and the neck pillow being selectively arranged between a pillow-blanket configuration and a storage configuration, wherein the first wrap panel, the second wrap panel, the neck pillow, and the controller is positioned outside the bag body as the pillow-blanket configuration, and wherein the first wrap panel, the second wrap panel, the neck pillow, and the controller is positioned inside the bag body as the storage configuration, and wherein the tote bag is configured to convert the storage configuration into the pillow-blanket configuration by turning the tote bad inside out and vice versa.

2. The apparatus capable of transforming between a sleep aid and a tote bag as claimed in claim 1 comprising:
a first hand-receiving pocket;
a second hand-receiving pocket;
the first hand-receiving pocket and the second hand-receiving pocket each comprising a pocket body and a pocket opening;
the pocket body of the first hand-receiving pocket being integrated into the first wrap panel;
the pocket opening of the first hand-receiving pocket and the first lengthwise edge being positioned opposite to each other across the first wrap panel;
the pocket body of the second hand-receiving pocket being integrated into the second wrap panel; and
the pocket opening of the second hand-receiving pocket and the second lengthwise edge being positioned opposite to each other across the second wrap panel.

3. The apparatus capable of transforming between a sleep aid and a tote bag as claimed in claim 1 comprising:
the neck pillow comprising a first side cushioning section, a center cushioning section, and a second side cushioning section;
the center cushioning section being hingedly connected along the widthwise edge;
the first side cushioning section being hingedly connected adjacent to the center cushioning section; and
the second side cushioning section being hingedly connected adjacent to the center cushioning section, opposite to the first side cushioning section.

4. The apparatus capable of transforming between a sleep aid and a tote bag as claimed in claim 3 comprising:
a chin strap;
the chin strap comprising a first strap section and a second strap section;
the first strap section being terminally connected to the first side cushioning section, opposite to the center cushioning section; and
the second strap section being terminally connected to the second side cushioning section, opposite to the center cushioning section.

5. The apparatus capable of transforming between a sleep aid and a tote bag as claimed in claim 3 comprising:
an eye mask;
a mask fastening mechanism;
the eye mask comprising a first mask end and a second mask end;
the mask fastening mechanism comprising a first interlocking piece and a second interlocking piece;
the first mask end being connected onto the first side cushioning section, opposite to the center cushioning section;
the first interlocking piece being connected onto the second mask end; and
the second interlocking piece being connected onto the second side cushioning section, opposite to the center cushioning section.

6. The apparatus capable of transforming between a sleep aid and a tote bag as claimed in claim 1 comprising:
a shoulder strap;
the shoulder strap comprising a first strap end and a second strap end;
the first strap end being connected onto the bag body, adjacent to the first lengthwise edge;
the second strap end being connected onto the bag body, adjacent to the second lengthwise edge; and
the shoulder strap being positioned across the widthwise opening.

7. The apparatus capable of transforming between a sleep aid and a tote bag as claimed in claim 1 comprising:
the plurality of heating devices comprising a bag heating device, a first panel heating device, a second panel heating device, and a pillow heating device;
the bag heating device being integrated into the bag body;
the first panel heating device being integrated into the first wrap panel;
the second panel heating device being integrated into the second wrap panel; and
the pillow heating device being integrated into the neck pillow.

8. The apparatus capable of transforming between a sleep aid and a tote bag as claimed in claim 1 comprising:
a closure flap;
the closure flap comprising a fixed flap edge and a free flap edge;
the fixed flap edge and the free flap edge being positioned opposite to each other across the closure flap; and
the fixed flap edge being connected onto the proximal bag panel, adjacent to the widthwise opening.

9. The apparatus capable of transforming between a sleep aid and a tote bag as claimed in claim 8 comprising:
a flap strap;
a strap-receiving buckle;
the flap strap comprising a fixed strap end and a free strap end;
the fixed strap end being connected onto the proximal bag panel, adjacent to the fixed flap edge; and
the strap-receiving buckle being connected onto the distal bag panel, adjacent to the widthwise opening.

10. The apparatus capable of transforming between a sleep aid and a tote bag as claimed in claim 1 comprising:
a volumetric-reduction fastening mechanism;
the volumetric-reduction fastening mechanism comprising a plurality of first interlocking pieces and a plurality of second interlocking pieces;
the plurality of first interlocking pieces being connected across the proximal bag panel in between the first lengthwise edge and the second lengthwise edge;
the plurality of first interlocking pieces being positioned adjacent to the widthwise opening;

the plurality of second interlocking pieces being connected across the proximal bag panel in between the first lengthwise edge and the second lengthwise edge; and the plurality of second interlocking pieces being positioned adjacent to the widthwise edge.

11. The apparatus capable of transforming between a sleep aid and a tote bag as claimed in claim 1 comprising:

a power terminal;

the power terminal being positioned offset to the controller; and the power terminal being electrically connected to the controller and each of the plurality of heating devices.

12. An apparatus capable of transforming between a sleep aid and a tote bag comprising:

a tote bag;

a plurality of heating devices;

a controller;

a power terminal;

an eye mask;

a mask fastening mechanism;

a chin strap;

the tote bag comprising a bag body, a first wrap panel, a second wrap panel, and a neck pillow;

the eye mask comprising a first mask end and a second mask end;

the mask fastening mechanism comprising a first interlocking piece and a second interlocking piece;

the chin strap comprising a first strap section and a second strap section;

the bag body comprising a proximal bag panel, a distal bag panel, a first lengthwise edge, a second lengthwise edge, a widthwise opening, and a widthwise edge;

the neck pillow comprising a first side cushioning section, a center cushioning section, and a second side cushioning section;

the plurality of heating devices comprising a bag heating device, a first panel heating device, a second panel heating device, and a pillow heating device;

the first lengthwise edge and the second lengthwise edge being positioned opposite to each other about the bag body;

the proximal bag panel, the distal bag panel, and the first wrap panel being connected along the first lengthwise edge;

the proximal bag panel, the distal bag panel, and the second wrap panel being connected along the second lengthwise edge;

the widthwise opening and the widthwise edge being positioned opposite to each other about the bag body;

the proximal bag panel, the distal bag panel, and the neck pillow being connected along the widthwise edge;

the plurality of heating devices being integrated throughout the tote bag;

the controller being electronically connected to each of the plurality of heating devices;

the bag heating device being integrated into the bag body;

the first panel heating device being integrated into the first wrap panel;

the second panel heating device being integrated into the second wrap panel;

the pillow heating device being integrated into the neck pillow;

the power terminal being positioned offset to the controller;

the power terminal being electrically connected to the controller and each of the plurality of heating devices;

the bag body, the first wrap panel, the second wrap panel, and the neck pillow being selectively arranged between a pillow-blanket configuration and a storage configuration, wherein the first wrap panel, the second wrap panel, the neck pillow, and the controller is positioned outside the bag body as the pillow-blanket configuration, and wherein the first wrap panel, the second wrap panel, the neck pillow, and the controller is positioned inside the bag body as the storage configuration, and wherein the tote bag is configured to convert the storage configuration into the pillow-blanket configuration by turning the tote bad inside out and vice versa;

the center cushioning section being hingedly connected along the widthwise edge;

the first side cushioning section being hingedly connected adjacent to the center cushioning section;

the second side cushioning section being hingedly connected adjacent to the center cushioning section, opposite to the first side cushioning section;

the first strap section being terminally connected to the first side cushioning section, opposite to the center cushioning section;

the second strap section being terminally connected to the second side cushioning section, opposite to the center cushioning section;

the first mask end being connected onto the first side cushioning section, opposite to the center cushioning section;

the first interlocking piece being connected onto the second mask end; and the second interlocking piece being connected onto the second side cushioning section, opposite to the center cushioning section.

13. The apparatus capable of transforming between a sleep aid and a tote bag as claimed in claim 12 comprising:

a first hand-receiving pocket;

a second hand-receiving pocket;

the first hand-receiving pocket and the second hand-receiving pocket each comprising a pocket body and a pocket opening;

the pocket body of the first hand-receiving pocket being integrated into the first wrap panel;

the pocket opening of the first hand-receiving pocket and the first lengthwise edge being positioned opposite to each other across the first wrap panel;

the pocket body of the second hand-receiving pocket being integrated into the second wrap panel; and the pocket opening of the second hand-receiving pocket and the second lengthwise edge being positioned opposite to each other across the second wrap panel.

14. The apparatus capable of transforming between a sleep aid and a tote bag as claimed in claim 12 comprising:

a closure flap;

a flap strap;

a strap-receiving buckle;

the closure flap comprising a fixed flap edge and a free flap edge;

the flap strap comprising a fixed strap end and a free strap end;

the fixed flap edge and the free flap edge being positioned opposite to each other across the closure flap;

the fixed flap edge being connected onto the proximal bag panel, adjacent to the widthwise opening;

the fixed strap end being connected onto the proximal bag panel, adjacent to the fixed flap edge; and the strap-receiving buckle being connected onto the distal bag panel, adjacent to the widthwise opening.

15. The apparatus capable of transforming between a sleep aid and a tote bag as claimed in claim 12 comprising:
- a shoulder strap;
- a volumetric-reduction fastening mechanism;
- the volumetric-reduction fastening mechanism comprising a plurality of first interlocking pieces and a plurality of second interlocking pieces;
- the shoulder strap comprising a first strap end and a second strap end;
- the plurality of first interlocking pieces being connected across the proximal bag panel in between the first lengthwise edge and the second lengthwise edge;
- the plurality of first interlocking pieces being positioned adjacent to the widthwise opening;
- the plurality of second interlocking pieces being connected across the proximal bag panel in between the first lengthwise edge and the second lengthwise edge;
- the plurality of second interlocking pieces being positioned adjacent to the widthwise edge;
- the first strap end being connected onto the bag body, adjacent to the first lengthwise edge;
- the second strap end being connected onto the bag body, adjacent to the second lengthwise edge; and
- the shoulder strap being positioned across the widthwise opening.

* * * * *